United States Patent
Makino

(10) Patent No.: US 10,856,722 B2
(45) Date of Patent: Dec. 8, 2020

(54) IMAGE PROCESSING APPARATUS AND ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

(*) Notice: Subject to any disclaimer, the term of this patent is extended or adjusted under 35 U.S.C. 154(b) by 352 days.

(21) Appl. No.: 15/556,425

(22) PCT Filed: Jul. 18, 2017

(86) PCT No.: PCT/IB2017/054322
§ 371 (c)(1),
(2) Date: Sep. 7, 2017

(87) PCT Pub. No.: WO2017/208216
PCT Pub. Date: Dec. 7, 2017

(65) Prior Publication Data
US 2018/0184889 A1    Jul. 5, 2018

(30) Foreign Application Priority Data

Jun. 2, 2016 (JP) ................................ 2016-110888

(51) Int. Cl.
*A61B 1/00* (2006.01)
*A61B 1/06* (2006.01)
(Continued)

(52) U.S. Cl.
CPC ...... *A61B 1/00009* (2013.01); *A61B 1/00186* (2013.01); *A61B 1/045* (2013.01);
(Continued)

(58) Field of Classification Search
CPC .............. A61B 1/0004; A61B 1/00009; A61B 1/00045; A61B 1/0005; A61B 1/00163;
(Continued)

(56) References Cited

U.S. PATENT DOCUMENTS 5,833,617 A * 11/1998 Hayashi ............ A61B 1/00009
600/476
8,643,710 B2 2/2014 Ono et al.
(Continued)

FOREIGN PATENT DOCUMENTS

JP    2004-321244    11/2004
JP    2010-035637    2/2010
(Continued)

OTHER PUBLICATIONS

Office Action from Japan Patent Office (JPO) in Japanese Patent Appl. No. 2016-110888, dated Aug. 21, 2018.
(Continued)

*Primary Examiner* — Ryan N Henderson
(74) *Attorney, Agent, or Firm* — Greenblum & Bernstein, P.L.C.

(57) ABSTRACT

Provided are an image processing apparatus and an electronic endoscope system that can acquire an observation image that is natural overall and has excellent visibility, while highlighting characteristic parts such as affected parts and parts that are to be examined. A normal observation image captured using normal light and a narrow-band observation image captured using narrow-band light that has a bandwidth narrower than that of normal light are input to the observation image input unit. A characteristic part extraction unit extracts a characteristic part that is included in a narrow-band observation image. A highlight display unit displays a single image in which a part of the normal observation image, the part corresponding to a characteristic part that is included in the narrow-band observation image, is highlighted using the characteristic part.

6 Claims, 4 Drawing Sheets

(51) Int. Cl.
*A61B 1/05* (2006.01)
*G06T 7/00* (2017.01)
*A61B 1/045* (2006.01)
*G02B 23/24* (2006.01)

(52) U.S. Cl.
CPC .............. *A61B 1/05* (2013.01); *A61B 1/0638* (2013.01); *A61B 1/0646* (2013.01); *A61B 1/0669* (2013.01); *G02B 23/2469* (2013.01); *G06T 7/00* (2013.01); *G06T 7/0012* (2013.01)

(58) Field of Classification Search
CPC ... A61B 1/00172; A61B 1/00186; A61B 1/04; A61B 1/043; A61B 1/045; A61B 1/05; A61B 1/0638; A61B 1/0646; A61B 1/0653; A61B 1/0669; A61B 1/063; A61B 1/0059; A61B 1/0071; G02B 23/2407; G02B 23/2415; G02B 23/2423; G02B 23/243; G02B 23/2438; G02B 23/2446; G02B 23/2453; G02B 23/2461; G02B 23/2469; G06T 7/00; G06T 7/0012; G06T 7/0014; G06T 7/0016; H04N 5/33; H04N 5/332

See application file for complete search history.

(56) References Cited

U.S. PATENT DOCUMENTS

| | | | |
|---|---|---|---|
| 8,913,111 B2 | 12/2014 | Takahashi | |
| 9,028,396 B2* | 5/2015 | Minetoma | A61B 1/05 600/109 |
| 9,031,294 B2* | 5/2015 | Nosato | G06T 7/11 382/128 |
| 2003/0197793 A1* | 10/2003 | Mitsunaga | H01L 27/14621 348/222.1 |
| 2004/0109068 A1* | 6/2004 | Mitsunaga | H04N 5/3651 348/222.1 |
| 2005/0134698 A1* | 6/2005 | Schroeder | H04N 9/04515 348/218.1 |
| 2005/0134712 A1* | 6/2005 | Gruhlke | H04N 9/045 348/272 |
| 2009/0312629 A1* | 12/2009 | Razzaque | A61B 5/7445 600/426 |
| 2010/0030021 A1* | 2/2010 | Minai | A61B 1/041 600/109 |
| 2010/0053213 A1* | 3/2010 | Ishida | G06F 19/321 345/629 |
| 2011/0063427 A1* | 3/2011 | Fengler | A61B 1/042 348/65 |
| 2011/0235877 A1 | 9/2011 | Morita | |
| 2011/0285879 A1* | 11/2011 | Hatakeyama | H04N 9/646 348/241 |
| 2012/0327205 A1* | 12/2012 | Takahashi | G02B 23/2461 348/65 |
| 2013/0039562 A1* | 2/2013 | Watanabe | A61B 1/00009 382/132 |
| 2013/0293704 A1* | 11/2013 | Imamura | G01C 3/08 348/135 |
| 2014/0316195 A1* | 10/2014 | Kaku | A61B 1/00009 600/104 |
| 2015/0305607 A1 | 10/2015 | Morita | |
| 2016/0089012 A1* | 3/2016 | Aoyama | G06T 7/0012 348/71 |
| 2016/0296106 A1 | 10/2016 | Shoji | |
| 2017/0209031 A1* | 7/2017 | Nakamura | A61B 1/04 |
| 2017/0251912 A1* | 9/2017 | Kato | A61B 1/0005 |

FOREIGN PATENT DOCUMENTS

| | | |
|---|---|---|
| JP | 2011-194111 | 10/2011 |
| JP | 2013-150712 | 8/2013 |
| JP | 2015-223249 | 12/2015 |

OTHER PUBLICATIONS

U.S. Appl. No. 15/556,420 to Takao Makino, filed Sep. 7, 2017.
International Search Report (ISR) and Written Opinion from International Searching Authority (Japan Patent Office) in International Pat. Appl. No. PCT/IB2017/054322, dated Sep. 26, 2017, together with an English language copy of the ISR.
Office Action issued in Germany Counterpart Patent Appl. No. 112017000023.8, dated Aug. 26, 2020.

* cited by examiner

NORMAL LIGHT

NARROW-BAND LIGHT

IMAGE PROCESSING APPARATUS AND ELECTRONIC ENDOSCOPE SYSTEM

TECHNICAL FIELD

The present invention relates to an image processing apparatus and an electronic endoscope system.

BACKGROUND ART

Patent Documents 1 and 2 disclose an electronic endoscope system that acquires a normal observation image captured using normal light and a narrow-band observation image captured using narrow-band light that has a bandwidth narrower than that of normal light, and displays the images side by side on one screen.

PRIOR ART DOCUMENTS

Patent Documents

Patent Document 1: JP 2004-321244A
Patent Document 2: JP 2015-223249A

SUMMARY OF INVENTION

Problem to be Solved by Invention

However, since characteristic parts such as affected parts and parts that are to be examined are highlighted in a narrow-band observation image, it is inevitable that a narrow-band observation image has an unnatural appearance that is significantly different from the appearance of a normal observation image in terms of colors and so on. Also, since a normal observation image and a narrow-band observation image are divided in two on the screen, each image has a smaller size, which degrades visibility.

The present invention is made based on awareness of the problems above, and one object thereof is to provide an image processing apparatus and an electronic endoscope system that can acquire an observation image that is natural overall and has excellent visibility, while highlighting characteristic parts such as affected parts and parts that are to be examined.

Means for Solving Problem

An image processing apparatus according to one aspect of the present invention includes: an observation image input unit to which a normal observation image captured using normal light and a narrow-band observation image captured using narrow-band light that has a bandwidth narrower than that of normal light are input; a characteristic part extraction unit that extracts a characteristic part that is included in the narrow-band observation image; and a highlight display unit that displays a single image in which a part of the normal observation image, the part corresponding to a characteristic part that is included in the narrow-band observation image, is highlighted using the characteristic part.

An electronic endoscope system according to one aspect of the present invention includes: an electronic endoscope that acquires a normal observation image captured using normal light and a narrow-band observation image captured using narrow-band light that has a bandwidth narrower than that of normal light; and an image processing apparatus that performs image processing on the normal observation image and the narrow-band observation image, wherein the image processing apparatus includes: a characteristic part extraction unit that extracts a characteristic part that is included in the narrow-band observation image; and a highlight display unit that displays a single image in which a part of the normal observation image, the part corresponding to a characteristic part that is included in the narrow-band observation image, is highlighted using the characteristic part.

The highlight display unit can display the single image in which the part of the normal observation image, the part corresponding to the characteristic part that is included in the narrow-band observation image, is combined with the characteristic part.

The characteristic part extraction unit can extract, as the characteristic part, a surface layer characteristic component that is obtained by subtracting a B component of the narrow-band observation image from an R component of the normal observation image, and the highlight display unit can subtract the surface layer characteristic component from a G component and a B component of the normal observation image.

The characteristic part extraction unit can extract, as the characteristic part, a deep layer characteristic component that is obtained by subtracting a G component of the narrow-band observation image from the R component of the normal observation image, and further subtracting the surface layer characteristic component therefrom, and the highlight display unit can subtract the deep layer characteristic component from the R component of the normal observation image.

The highlight display unit can display the single image in which the part of the normal observation image, the part corresponding to the characteristic part that is included in the narrow-band observation image, is replaced with the characteristic part.

In the present description, modes in which the highlight display unit displays a highlighted single image includes a mode in which a part of a normal observation image, the part corresponding to a characteristic part that is included in a narrow-band observation image, is combined with the characteristic part, and a mode in which the part of the normal observation image, the part corresponding to the characteristic part that is included in the narrow-band observation image, is replaced with the characteristic part. That is, "to highlight" is used as a concept that includes "to combine" and "to replace".

Advantageous Effects of Invention

The present invention can provide an image processing apparatus and an electronic endoscope system that can acquire an observation image that is natural overall and has excellent visibility, while highlighting characteristic parts such as affected parts and parts that are to be examined.

DESCRIPTION OF EMBODIMENTS

The following describes an electronic endoscope system 1 according to an embodiment of the present invention with reference to FIGS. 1 to 5. The electronic endoscope system 1 includes an electronic endoscope 10, a processor (an image processing apparatus and a light source apparatus) 20, and a monitor 30.

Figure 1:
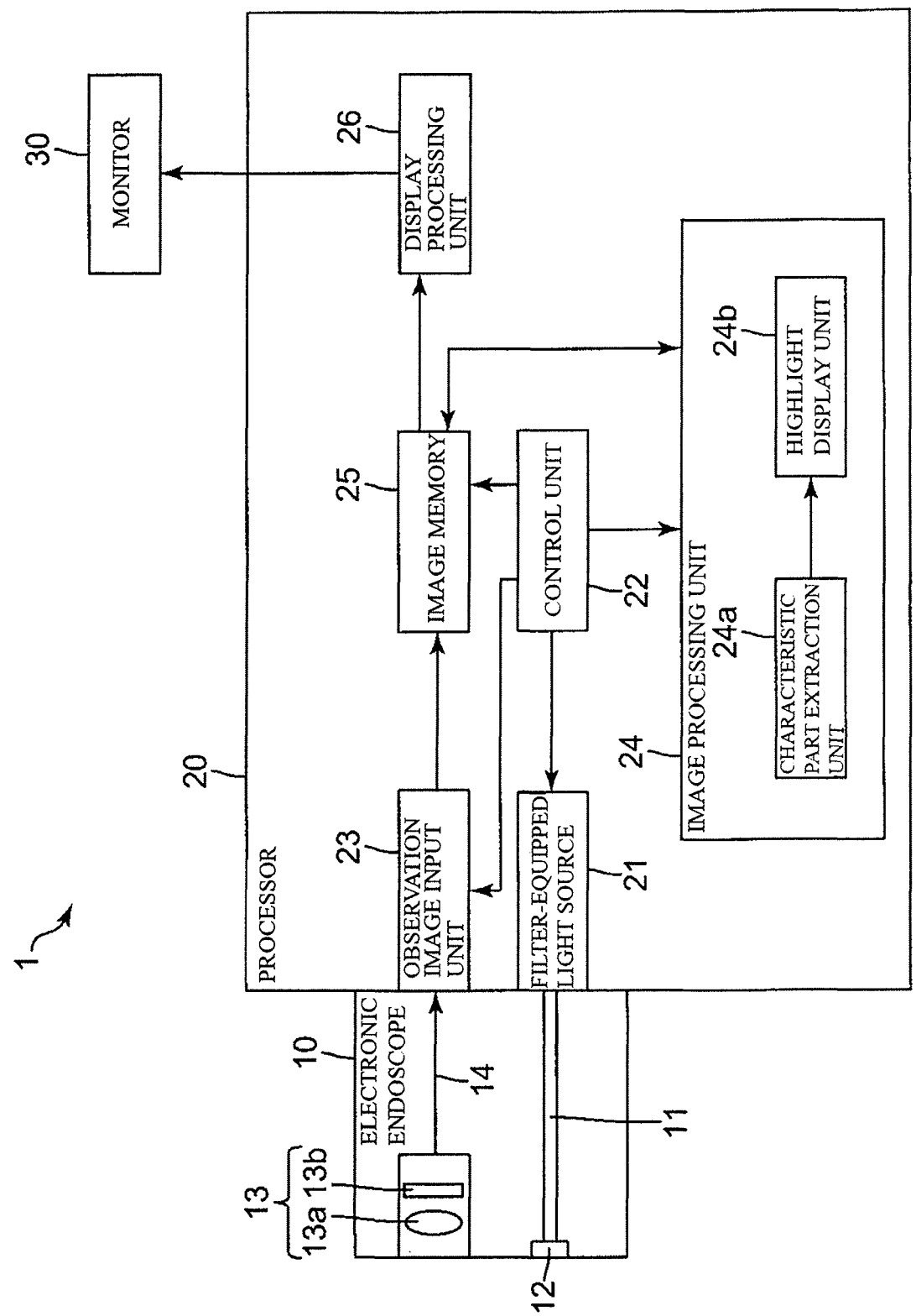
FIG. 1 is a block diagram showing a configuration of an electronic endoscope system according to an embodiment of the present invention.

Although details of the shape of the electronic endoscope 10 are omitted from FIG. 1, the electronic endoscope 10 includes a grip and control portion that is to be gripped by an operator, an insertion portion that is flexible and extends from the grip and control portion, a universal tube that extends from the grip and control portion in a direction away from the insertion portion, and a connector that is provided at the leading end of the universal tube.

Light-guide fibers 11 are built into the electronic endoscope 10. The light-guide fibers 11 extend to the inside of the connector via the insertion portion, the grip and operation portion, and the universal tube of the electronic endoscope 10. The connector of the electronic endoscope 10 is connected to a connector of the processor 20, and thus the electronic endoscope 10 and the processor 20 are optically connected to each other. Illumination light (normal light or narrow-band light described below) from a filter-equipped light source 21, which is built into the processor 20, is guided inside the light-guide fibers 11, and is emitted outward from an illumination lens 12, which is provided at the leading end of the insertion portion of the electronic endoscope 10, according to a predetermined light distribution pattern.

The filter-equipped light source 21 includes a high-intensity lamp (e.g. a xenon lamp, a halogen lamp, a mercury lamp, or a metal halide lamp) that emits white light that includes wavelength bands respectively corresponding to R (Red), G (Green), and B (blue). The filter-equipped light source 21 also includes a filter unit that is located on the light path of the white light emitted from the high-intensity lamp. The filter unit includes a rotary filter turret that is provided with a filter for the color white, which allows white light from the high-intensity lamp to pass, thereby generating normal light, and a narrow-band filter, which narrows the wavelength band of the white light emitted from the high-intensity lamp, thereby generating narrow-band light. The narrow-band filter has a spectral transmittance with a narrow width at half maximum, for each of the R, G and B wavelength bands. The rotary filter turret of the filter unit is driven to rotate, and thus white light from the high-intensity lamp alternatingly passes through the filter for the color white and the narrow-band filter, and normal light and narrow-band light that has a bandwidth narrower than that of normal light are alternatingly emitted from the filter-equipped light source 21. The wavelength band of narrow-band light can be set as desired as long as it is narrower than the wavelength band of normal light. For example, narrow-band light may have a wavelength band that matches the spectral properties of hemoglobin. The filter-equipped light source 21 is well known as disclosed in Patent Document 2 above, for example, and therefore a further detailed description thereof is omitted.

An imaging unit 13 is provided at the leading end of the insertion portion of the electronic endoscope 10. The imaging unit 13 is composed of a plurality of constituent elements that include an objective lens 13a and a CCD 13b that captures a subject image that has passed through the objective lens 13a, and are integrated into one piece using a resin material such as an epoxy resin. The CCD 13b alternatingly acquires a normal observation image signal and a narrow-band observation image signal that are respectively based on normal light and narrow-band light that are alternatingly emitted from the filter-equipped light source 21 via the light-guide fibers 11 and the illumination lens 12. The normal observation image signal and the narrow-band observation image signal are transmitted to the processor 20 via a signal transmission cable 14.

The processor 20 includes a control unit 22, an observation image input unit (an image input processing unit) 23, an image processing unit (a computation unit) 24, an image memory 25, and a display processing unit 26. The control unit 22 totally controls all of the constituent elements of the processor 20.

The observation image input unit 23 performs input processing on the normal observation image signal and the narrow-band observation image signal transmitted from the signal transmission cable 14 of the electronic endoscope 10, to input the signals as a normal observation image and a narrow-band observation image.

The image processing unit 24 performs image processing on the normal observation image and the narrow-band observation image input to the observation image input unit 23. The image processing unit 24 includes a characteristic part extraction unit (an image feature calculation unit) 24a and a highlight display unit (a display result creation unit) 24b.

The characteristic part extraction unit 24a extracts characteristic parts that are included in a narrow-band observation image input to the observation image input unit 23. More specifically, the characteristic part extraction unit 24a extracts, as a characteristic part of the narrow-band observation image, a surface layer characteristic component that is obtained by subtracting the B component of the narrow-band observation image from the R component of the normal observation image input to the observation image input unit 23. Furthermore, the characteristic part extraction unit 24a extracts, as a characteristic part of the narrow-band observation image, a deep layer characteristic component that is obtained by subtracting the G component of the narrow-band observation image from the R component of the normal observation image input to the observation image input unit 23, and further subtracting the above-described surface layer characteristic component therefrom.

The highlight display unit 24b combines the characteristic part of the narrow-band observation image extracted by the characteristic part extraction unit 24a, with a part, which corresponds to the characteristic part, of the normal observation image input to the observation image input unit 23, thereby generating a single combined observation image (a single image) in which the characteristic part is highlighted. More specifically, the highlight display unit 24b subtracts the surface layer characteristic component extracted by the characteristic part extraction unit 24a, from the G component and the B component of the normal observation image input to the observation image input unit 23, and also subtracts the deep layer characteristic component extracted by the characteristic part extraction unit 24a, from the R component of the normal observation image input to the observation image input unit 23.

Figure 2:
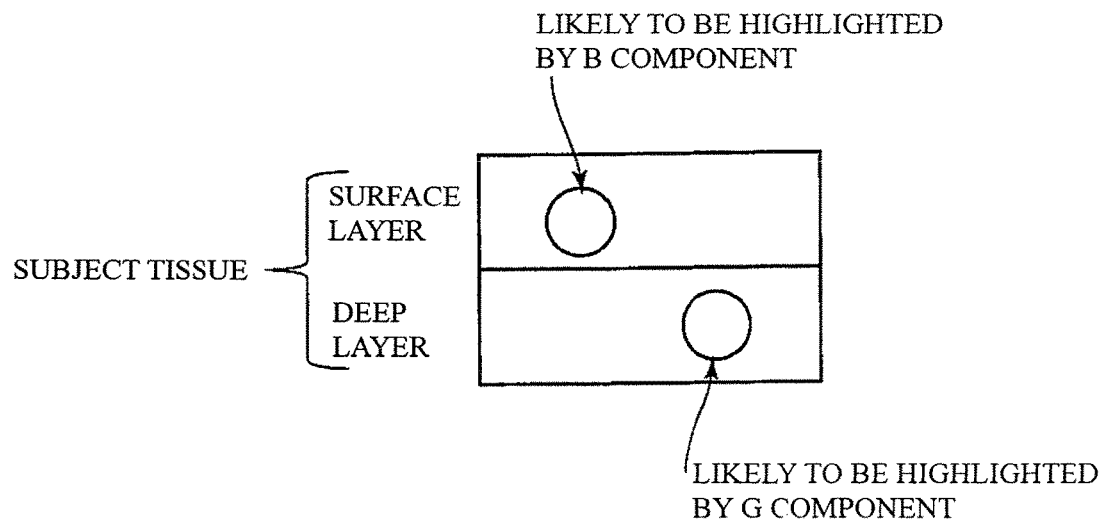
FIG. 2 is a diagram showing blood vessels, which are characteristic parts in a surface layer and a deep layer of a subject tissue in a narrow-band observation image.
Figure 3A:
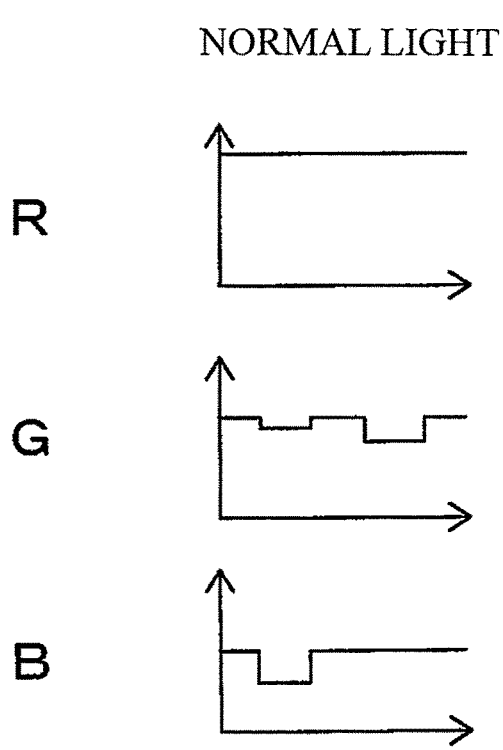
FIGS. 3A and 3B are diagrams showing R, G, and B wavelength components corresponding to surface layer information and deep layer information when normal light and narrow-band light are used.
Figure 3B:
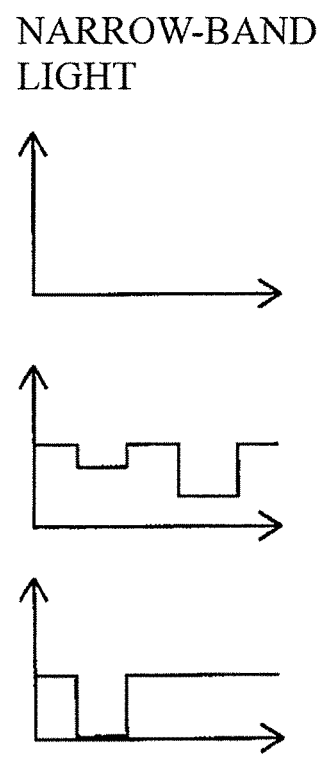

FIG. 2 is a diagram showing blood vessels, which are characteristic parts in the surface layer and the deep layer of subject tissue in a narrow-band observation image. FIGS. 3A and 3B are diagrams showing R, G, and B wavelength components corresponding to surface layer information and deep layer information when normal light and narrow-band light are used. In an observation image obtained using an endoscope, the R component is a dominant color component and has the smallest feature value, and therefore it can be said that the G component and the B component are the color components that are suitable for the purpose of highlighting a feature. A narrow-band observation image includes a large amount of information regarding the surface layer of tissue in the B component, and a large amount of information regarding the deep layer of tissue in the G component. Therefore, blood vessels in the surface layer of tissue are responsive to (absorb a large amount of) light that has the wavelength of the B component, and are likely to be highlighted by the B component, and blood vessels in the deep layer of tissue are responsive to (absorb a large amount of) light that has the wavelength of the G component, and are likely to be highlighted by the G component. Therefore, by selectively using the above-described surface layer characteristic component and deep layer characteristic component, it is possible to highlight the vessels in the surface layer of tissue and the vessels in the deep layer of tissue such that they appear different from each other.

Figure 4:
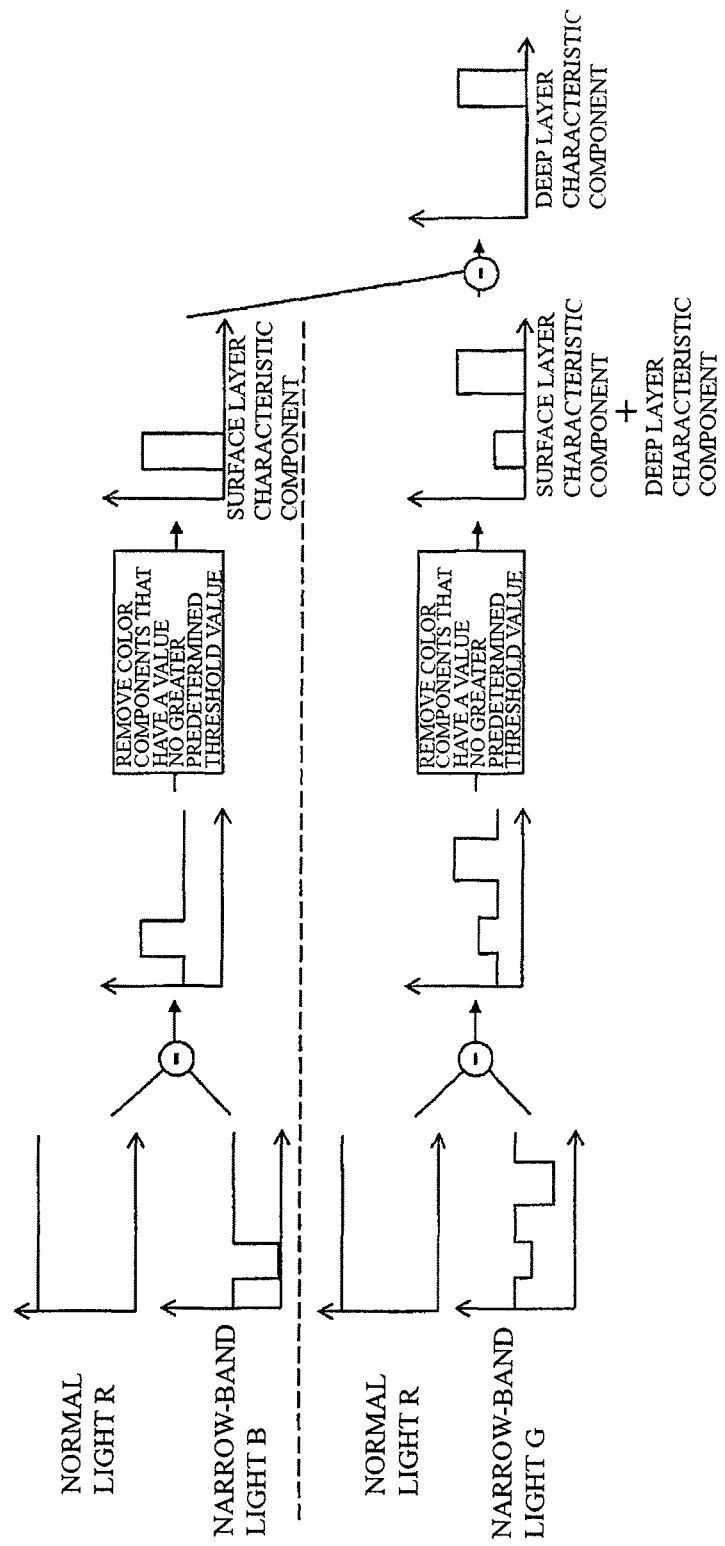
FIG. 4 is a diagram showing a method for computing a surface layer characteristic component and a deep layer characteristic component.

FIG. 4 is a diagram showing a method for computing a surface layer characteristic component and a deep layer characteristic component. As seen from this drawing, the surface layer characteristic component is obtained by subtracting the B component of the narrow-band observation image from the R component of the normal observation image, and removing color components that have a value no greater than a predetermined threshold value, from the result of subtraction. Also, the deep layer characteristic component is obtained by subtracting the G component of the narrow-band observation image from the R component of the normal observation image, removing color components that have a value no greater than a predetermined threshold value, from the result of subtraction, to obtain the sum of the surface layer characteristic component and the deep layer characteristic component, and subtracting the above-described surface layer characteristic component from the sum. Thus, only the surface layer characteristic component and the deep layer characteristic component of the narrow-band observation image are extracted. For example, by subtracting the deep layer characteristic component, which is unlikely to affect the overall color or the like, from the R component of the normal observation image, which has a small feature value, and further subtracting the original surface layer characteristic component from the G component and the B component, it is possible to highlight the characteristic parts by only changing the color and contrast of the characteristic parts without changing the color and contrast of the normal observation image. Note that the predetermined threshold value may be a fixed value, and may be dynamically calculated and set based on, for example, the average of the values of the R, G, and B components. It is also possible to omit the processing performed to remove color components that have a value no greater than the predetermined threshold value (to set the threshold value to zero).

The image memory 25 stores a combined observation image (a single image) in which the characteristic parts of the narrow-band observation image have been highlighted by the image processing unit 24. The display processing unit 26 displays the combined observation image (the single image) stored in the image memory 25 on the monitor 30.

Figure 5:
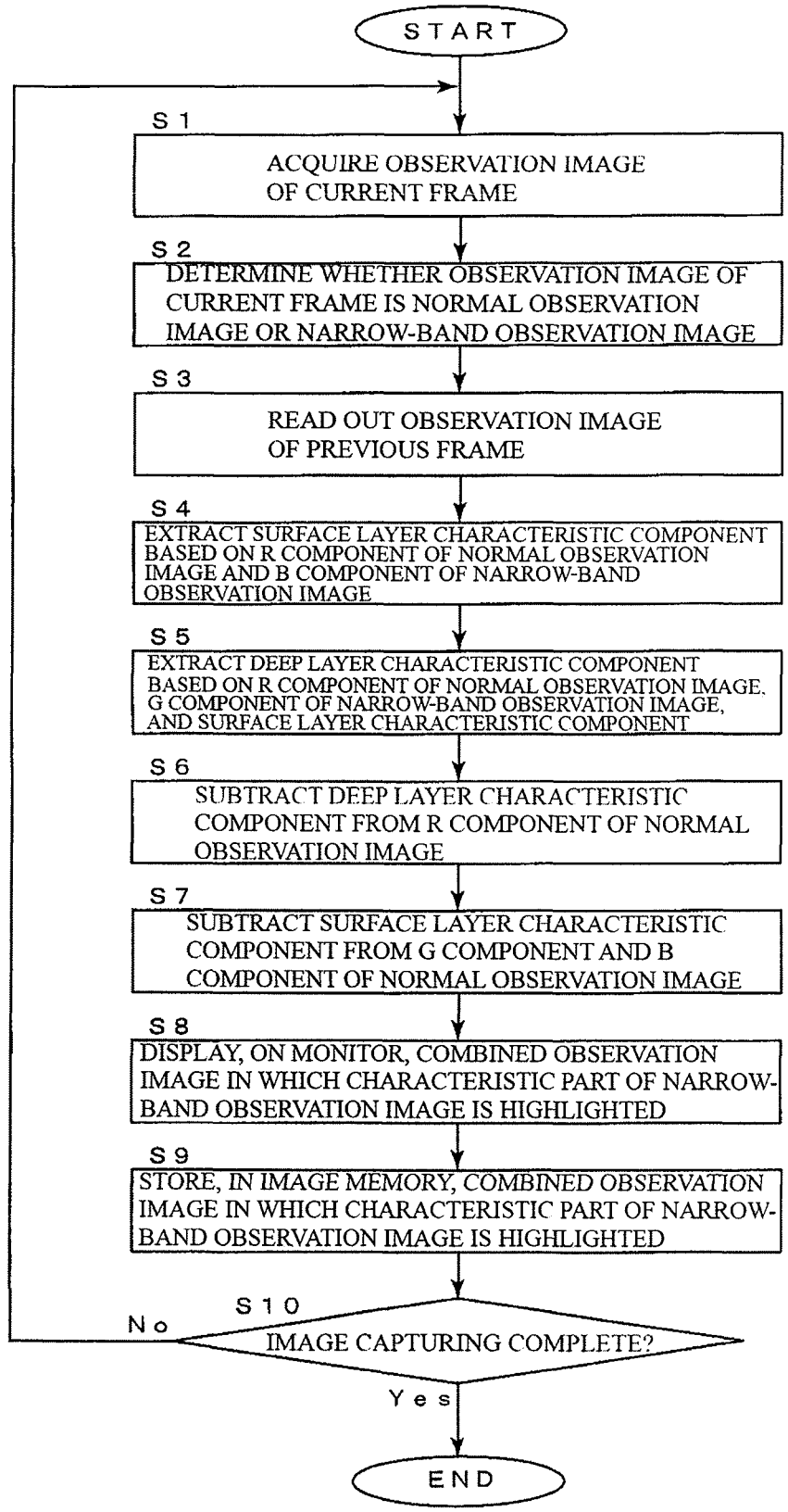
FIG. 5 is a flowchart showing image processing according to the embodiment of the present invention.

The following describes image processing performed by the electronic endoscope system 1 and the processor 20 according to the present embodiment with reference to the flowchart shown in FIG. 5.

In step S1, the image processing unit 24 acquires an observation image of the current frame.

In step S2, the image processing unit 24 determines whether the observation image of the current frame acquired in step S1 is a normal observation image or a narrow-band observation image. This determination processing is performed by, for example, detecting the rotational phase of the filter unit (the rotary filter turret) of the filter-equipped light source 21.

In step S3, the image processing unit 24 reads out the observation image of the previous frame, which is previous to the current frame from which the observation image was acquired in step S1. Since a normal observation image and a narrow-band observation image are alternatingly output one at each frame, the observation image of the current frame acquired in step S1 and the observation image of the previous frame read out in step S3 constitute one set composed of a normal observation image and a narrow-band observation image. Also, the normal observation image and the narrow-band observation image that constitute one set appear different only due to the wavelength bands of their irradiation light being different, and hence they can be regarded as substantially identical subject images. Furthermore, by using a normal observation image and a narrow-band observation image that constitute one set, it is possible to display a combined observation image (a single image) without lowering the frame rate.

In step S4, the characteristic part extraction unit 24a of the image processing unit 24 extracts (calculates) the surface layer characteristic component based on the R component of the normal observation image and the B component of the narrow-band observation image.

In step S5, the characteristic part extraction unit 24a of the image processing unit 24 extracts (calculates) the deep layer characteristic component based on the R component of the normal observation image and the G component of the narrow-band observation image as well as the surface layer characteristic component extracted in step S4.

In step S6, the highlight display unit 24b of the image processing unit 24 subtracts the deep layer characteristic component extracted in step S5, from the R component of the normal observation image.

In step S7, the highlight display unit 24b of the image processing unit 24 subtracts the surface layer characteristic component extracted in step S4, from the G component and the B component of the normal observation image.

The order in which the processing in step S6 and the processing in step S7 are performed can be determined as desired, and it is possible to simultaneously perform the processing in these steps.

In step S8, the display processing unit 26 displays, on the monitor 30, an observation image (a combined observation image, a single image) in which the characteristic parts of the narrow-band observation image have been highlighted by the image processing unit 24.

In step S9, the combined observation image in which the characteristic parts of the narrow-band observation image have been highlighted by the image processing unit 24 is stored in the image memory 25. The combined observation image stored in the image memory 25 will be externally saved after observation, and will be used as a material for more detailed diagnosis or explanation, for example.

In step S10, the processor 20 determines whether or not image capturing by the electronic endoscope 10 is complete. Upon the processor 20 determining that image capturing performed by the electronic endoscope 10 is complete (step S10: Yes), processing from step S1 to step S9 is terminated. Upon the processor 20 determining that image capturing performed by the electronic endoscope 10 is not complete (step S10: No), the processing loop from step S1 to step S9 is repeatedly performed.

As described above, in the electronic endoscope system 1 and the processor 20 according to the present embodiment, the characteristic part extraction unit 24a extracts a characteristic part that is included in a narrow-band observation image, and the highlight display unit 24b displays a single image in which a part of a normal observation image, which corresponds to the characteristic part included in the narrow-band observation image, is highlighted using the characteristic part. Therefore, it is possible to highlight characteristic parts such as affected parts and parts that are to be examined, and to perform treatment (an operation) or examination with high accuracy. In addition, parts other than the characteristic parts such as affected parts and parts that are to be examined are maintained so as to have the color and so on of the normal observation image, and the observation image with the highlighted parts is displayed in a large size on the entire screen. Thus, the observation image can be natural and can have excellent visibility overall. Also, images of two frames that have been successively captured are used to suppress a decrease in the frame rate to the minimum, and also from this point of view, natural image display is realized.

The embodiment above describes an example in which the highlight display unit 24b combines the characteristic part of the narrow-band observation image extracted by the characteristic part extraction unit 24a, with a part, which corresponds to the characteristic part, of the normal observation image input to the observation image input unit 23, thereby generating a combined observation image in which the characteristic part is highlighted.

Here, the method for generating the combined observation image employed by the highlight display unit 24b is not limited to the method described in the embodiment above, and various design changes are applicable. For example, it is possible to change the combination of the R, G, and B components and the combination of the addition and subtraction of the surface layer characteristic component and the deep layer characteristic component according to the purpose of the observation image, and it is possible to increase or reduce the surface layer characteristic component and the deep layer characteristic component by multiplying them by a given coefficient before performing addition or subtraction. Also, it is possible to employ various kinds of computation such as multiplication and division as appropriate.

Furthermore, it is also possible for the highlight display unit 24b to replace a part of the normal observation image input to the observation image input unit 23, the part corresponding to the characteristic part of the narrow-band observation image extracted by the characteristic part extraction unit 24a, with the characteristic part, thereby generating a partially-replaced observation image (a single image) in which the characteristic part is highlighted. In this mode, it is possible to further clarify the boundary between the characteristic part of the partially-replaced observation image and the other part.

INDUSTRIAL APPLICABILITY

The image processing apparatus and the electronic endoscope system according to the present invention can be preferably employed as an image processing apparatus and an electronic endoscope system in the field of medical endoscopes, for example.

DESCRIPTION OF REFERENCE SIGNS

1 Electronic Endoscope System
10 Electronic Endoscope
11 Light Guide Fibers
12 Illumination Lens
13 Imaging Unit
13a Objective Lens
13b CCD
14 Signal Transmission Cable
20 Processor (Image Processing Apparatus, Light Source Apparatus)
21 Filter-Equipped Light Source
22 Control Unit
23 Observation Image Input Unit (Image Input Processing Unit)
24 Image Processing Unit (Computation Unit)
24a Characteristic Part Extraction Unit (Image Feature Calculation Unit)
24b Highlight Display Unit (Display Result Creation Unit)
25 Image Memory
26 Display Processing Unit
30 Monitor

The invention claimed is:

1. An image processing apparatus including a processor, the processor configured to:
   capture an input normal observation image using normal light and an input narrow-band observation image using narrow-band light that has a bandwidth narrower than that of normal light;
   extract a characteristic part that is included in the narrow-band observation image, wherein, as the characteristic part, a surface layer characteristic component that is obtained by subtracting a Blue component of the narrow-band observation image from an Red component of the normal observation image is extracted; and
   display a single image in which a part of the normal observation image is highlighted, the part corresponding to a characteristic part of the normal observation image, wherein, in the single image in which the part of the normal observation image is highlighted, the part of the normal observation image corresponding to the characteristic part included in the narrow-band observation image is combined with the characteristic part of the normal observation image and the processor subtracts the surface layer characteristic component from a Green component and a Blue component of the normal observation image.

2. The image processing apparatus according to claim 1, as the extracted characteristic part, a deep layer characteristic component is obtained by subtracting a Green component of the narrow-band observation image from the Red component of the normal observation image, and the surface layer characteristic component is therefrom, and
the single image display comprises subtracting the deep layer characteristic component from the Red component of the normal observation image.

3. The image processing apparatus according to claim 1,
wherein the display comprises displaying the single image in which the part of the normal observation image is highlighted, wherein, the part corresponding to the characteristic part that is included in the narrow-band observation image, is replaced with the characteristic part.

4. An electronic endoscope system comprising:
an electronic endoscope that acquires a normal observation image captured using normal light and a narrow-band observation image captured using narrow-band light that has a bandwidth narrower than that of normal light; and
an image processing apparatus that performs image processing on the normal observation image and the narrow-band observation image,
wherein the image processing apparatus includes a processor, the processor configured to:
extract a characteristic part that is included in the narrow-band observation image, wherein, as the characteristic part, a surface layer characteristic component that is obtained by subtracting a Blue component of the narrow-band observation image from a Red component of the normal observation image is extracted; and
display a single image in which a part of the normal observation image is highlighted, the part corresponding to a characteristic part of the normal observation image, wherein, in the single image in which the part of the normal observation image is highlighted, the part of the normal observation image corresponding to the characteristic part that is included in the narrow-band observation image is combined with the characteristic part of the normal observation image and the surface layer characteristic component is subtracted from a Green component and a Blue component of the normal observation image.

5. The electronic endoscope system according to claim 4,
as the extracted characteristic part, a deep layer characteristic component that is obtained by subtracting a Green component of the narrow-band observation image from the Red component of the normal observation image, and the surface layer characteristic component is subtracted therefrom, and
the single image display comprises subtracting the deep layer characteristic component from the Red component of the normal observation image.

6. The electronic endoscope system according to claim 4,
wherein the display comprises displaying the single image in which the part of the normal observation image is highlighted, wherein, the part corresponding to the characteristic part that is included in the narrow-band observation image, is replaced with the characteristic part.

* * * * *